United States Patent [19]
Frostell et al.

[11] Patent Number: 5,427,797
[45] Date of Patent: Jun. 27, 1995

[54] SYSTEMIC EFFECTS OF NITRIC OXIDE INHALATION

[75] Inventors: Claes G. Frostell, Vallingby; Goran Hedenstierna, Djursholm; Marieann E. Hogman, Alunda, all of Sweden; Joseph Loscalzo, Dedham; Jonathan S. Stamler, Boston, both of Mass.

[73] Assignee: Brigham and Women's Hospital, Boston, Mass.

[21] Appl. No.: 43,653

[22] Filed: Apr. 6, 1993

[51] Int. Cl.$^6$ .......................... A61L 9/04; A61K 9/12
[52] U.S. Cl. ........................ 424/434; 424/44; 424/45; 514/826; 514/957
[58] Field of Search ............... 424/434, 44, 45; 514/826, 957

[56] References Cited

FOREIGN PATENT DOCUMENTS

92/10228  6/1992  WIPO .

OTHER PUBLICATIONS

"Inhaled Nitric Oxide Reverses Hypoxic Vasoconstriction in Lambs and Humans", Biol. Nitric Oxide, Proc. Int. Meet., 2nd, Meeting Date 1991, vol. 1, 363-4 1992.

*Primary Examiner*—Thurman K. Page
*Assistant Examiner*—Carlos Azpuru
*Attorney, Agent, or Firm*—Charles J. Herron; Elliot M. Olstein

[57] ABSTRACT

Nitric oxide or nitric oxide releasing or delivering compounds administered by the inhalation route to humans and animals in need thereof have a systemic and pulmonary effect of preventing or treating blood platelet aggregation and coagulation and thus, are useful for the prevention or treatment of systemic platelet aggregation, pulmonary emboli, angina pectoris and acute respiratory distress syndrome.

6 Claims, 1 Drawing Sheet

SYSTEMIC EFFECTS OF NITRIC OXIDE INHALATION

BACKGROUND OF THE INVENTION

Under physiologic conditions, nitric oxide (NO) is exceedingly unstable, reacting essentially instantaneously with oxygen, superoxide anion, and redox metals (Lancaster et al., *Proc. Natl. Acad. Sci. USA*, 87:1223-1227 (1990); Ignarro et al., *Circ. Res.* 65:1-21 (1989); and Gryglewski et al., *Nature* 320:454-456 (1986)).

The consequences of NO production in the lung are not known. However, it has been believed that potential beneficial bronchodilation effects of NO may be counterbalanced by generation of toxic nitrogen oxides that form readily under the high ambient concentration of oxygen and other reactive oxygen species. Introduction of NO into the lungs has been associated by some with adverse effects, which occur as a direct result of the particular chemical reactivity of the uncharged NO radical (NO·). These adverse effects create impediments to NO therapy which generally involves administration of NO·. For example, the reaction between NO·, and $O_2$ or reactive $O_2$ species which are present in high concentrations in the lung, generates highly toxic products, such as $NO_2$ and peroxynitrite. These reactions also result in the rapid inactivation of NO, thus allegedly eliminating any beneficial pharmacological effect. (Furchgott R. F. et al., I. Endothelium-Derived Relaxing Factors and Nitric Oxide; eds. Rubanyi G. M., pp. (1990); Gryglewski, R. J. et al., Nature 320:454-456 (1986)). Furthermore, NO· reacts with the redox metal site on hemoglobin to form methemoglobin, which inhibits oxygen-hemoglobin binding, thereby significantly reducing the oxygen-carrying capacity of the blood.

Nonetheless, some workers have convincingly demonstrated the value of NO therapy in bronchoconstriction and reversible pulmonary vasoconstriction. For example, Zapol and Frostell, PCT Publication No. WO 92/10228 discloses a method for treating or preventing bronchoconstriction, e.g., asthma or reversible pulmonary vasoconstriction, e.g., pulmonary hypertension, by inhalation of gaseous nitric oxide or nitric oxide-releasing compounds. Many such compounds are known. These investigators characterize the mammalian circulatory system as consisting of two separate circuits, the systemic circuit and the pulmonary circuit which are controlled by opposite sides of the heart. They report that (since NO gas which enters the bloodstream is rapidly inactivated by combination with hemoglobin) the bronchodilatory effects of inhaled NO are limited to the ventilated bronchi and the vasodilatory effects of inhaled NO are limited to those blood vessels near the site of NO passage into the blood stream: i.e., pulmonary microvessels. They conclude from this that an important advantage of their bronchodilating and pulmonary vasodilating methods is that one can selectively prevent or treat bronchospasm and/or pulmonary hypertension without producing a concomitant lowering of the systemic blood pressure to potentially dangerous levels and that, therefore, their method allows for effective reversal of pulmonary hypertension without the risk of underperfusion of vital organs, venous pooling, ischemia, and heart failure that may accompany systemic vasodilation. More specifically, they report that the rapid binding of NO to hemoglobin ensures that any vasodilatory action of inhaled NO is solely a local or selective effect in the blood vessels of the lung, with no concomitant vasodilation downstream in the systemic circulation.

SUMMARY OF THE INVENTION

In accordance with the present invention, it has been discovered for the first time that nitric oxide and its adducts, conjugates and other nitric oxide containing compounds widen administered by the inhalation route to an individual in need thereof, as the compound per se or as part of an adduct, conjugate or the like that releases nitric oxide (or an alternative redox form of nitrogen monoxide) are effective to prevent or treat both systemic and pulmonary emboli, effect systemic platelet deaggregation and are also effective as systemic anticoagulants.

DETAILED DESCRIPTION

Figure 1:
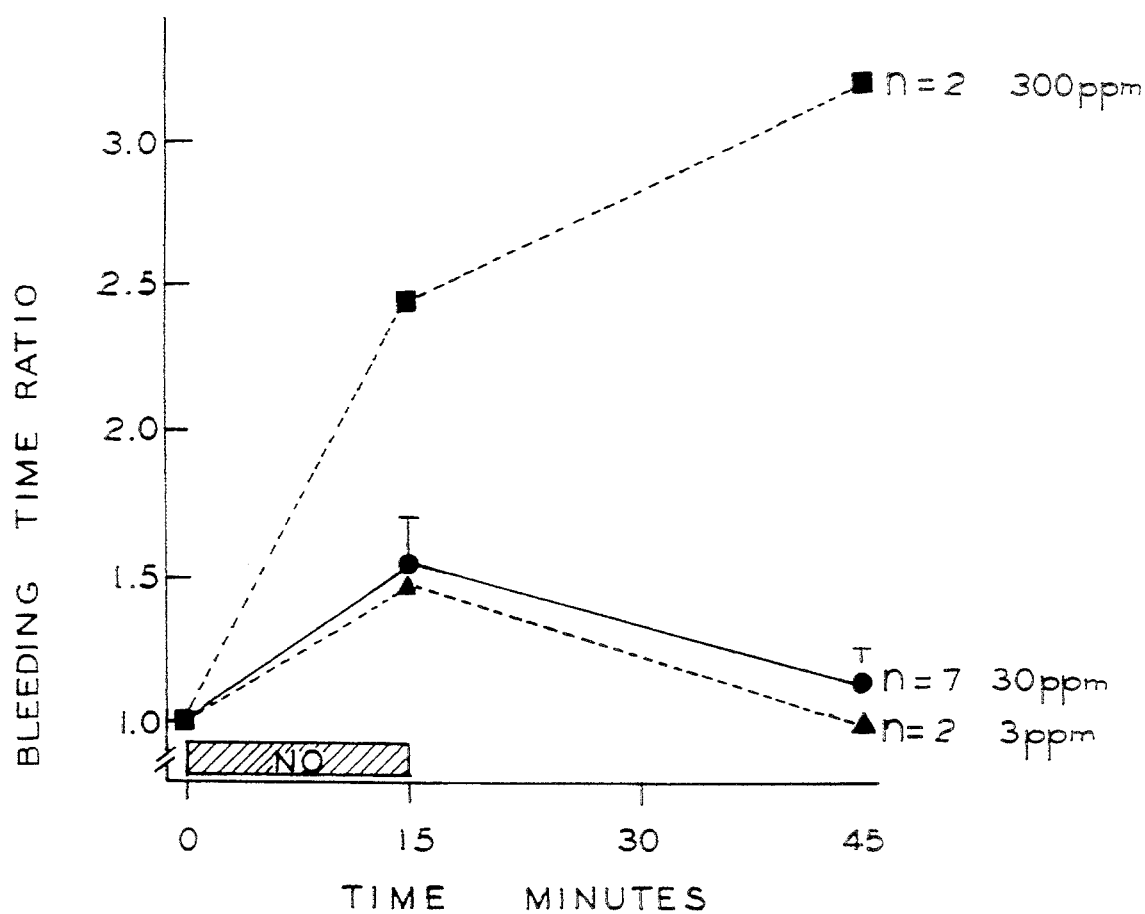
FIG. 1 is a graph showing bleeding time ratios in 10 rabbits exposed to 3 ppm NO (n=2), 30 ppm NO (n=7) or 300 ppm NO (n=2) for 15 minutes, and 15 minutes after terminating NO inhalation. Bleeding time ratio in parenthesis, the actual bleeding time divided with the baseline value.

Thus, in one aspect the invention relates to a method for the prevention or treatment of both systemic and pulmonary emboli, for preventing and reversing platelet aggregation and for anticoagulant therapy comprising administering by the inhalation route to a human or animal in need thereof a therapeutically effective amount of a compound (or pharmaceutical composition comprising such a compound) selected from the group consisting of nitric oxide and a compound that releases an effective amount of nitric oxide upon such administration.

Another aspect relates to a method for the prevention or treatment of angina pectoris and other unstable coronary syndromes comprising administering by the inhalation route to a human or animal in need thereof a therapeutically effective amount of a compound (or pharmaceutical composition comprising such a compound) selected from the group consisting of nitric oxide and a compound that releases an effective amount of nitric oxide upon such administration.

Another aspect relates to a method for the prevention or treatment of acute respiratory distress syndrome (ARDS) comprising administering by the inhalation route to an animal in need thereof a therapeutically effective amount of a compound (or pharmaceutical composition comprising such a compound) selected from the group consisting of nitric oxide and a compound that releases an effective amount of nitric oxide upon such administration. The therapeutic effect in this aspect is realized as a result of the fact that increased pressure causing the ARDS is in part the result of platelet aggregation which is reversed by such administration.

Nitric oxide releasing or delivering compounds which are useful in the methods of the invention include, but are not limited to, S-nitrosothiols (RSNO), S-nitroso-proteins, NONOnates [$X^--(NO)^-(NO)$], where $X^-$ is any base or nucleophile including compounds having N-hydroxy-N-nitrosoamino functionalities, iron nitrosyls such as nitroprusside and iron nitrosyls with thiolate ligands, thionitrites, thionitrates, sydnonimines such as SIN 1, furoxans, nitroglycerine, nitrosonium salts, organic nitrates, organic nitrites and related compounds. Examples of S-nitrosothiols include, but are not limited to S-nitroso-N-acetylcysteine, S-nitroso-captopril, S-nitroso-glutathione, S-nitroso-pantathoine derivatives, S-nitroso-penicilamine, long-chain lipophilic nitrosothiols, and, S-nitroso-cysteine, S-nitroso-homocysteine, S-nitroso-dithiols. Particular S-nitroso-proteins include S-nitroso-albumin.

Long carbon-chain lipophilic nitrosothiols are represented by the general formula $CH_3(CH_2)_xSNO$ where x is an integer. S-nitroso-dithiols possess an additional thiol group, and are represented by the general formula $HS(CH_2)_xSNO$ where x is an integer.

Examples of sydnonimines include, but are not limited to SYN-1 and 3-morpholinosydnonimine. Examples of organic nitrates include, but are not limited to, nitroglycerine, isosorbide dinitrate, erythritol tetranitrate and pentaerythritol tetranitrate. Iron-nitrosyl compounds are represented by the general formula $X_xFe_y(NO)_z$, wherein X is a low molecular weight or protein thiol, or a non-thiolate anion such as phosphate, ascorbate, anionic protein, or glycosaminoglycan, such as heparin sulfate, and x, y and z are integers that can be the same or different.

An additional embodiment of the invention relates to the methods of the invention in which the nitric oxide-delivering compound is administered as part of a pharmaceutical composition, comprising a pharmaceutically acceptable carrier.

Administration of the nitric oxide or nitric oxide releasing agent to the lung can be by hand held, portable ventilator, positive pressure respirator or other known devices and methods for respiratory administration.

The amount of the therapeutic of the invention which will be effective in the treatment of a particular disorder or condition will depend on the nature of the disorder or condition, and can be determined by standard clinical techniques. The precise dose to be employed in the formulation will also depend on the choice of compound and the seriousness of the disease or disorder, and should be decided according to the judgment of the practitioner and each patient's circumstances. However, suitable dosage ranges for respiratory administration are generally about 1.0 picograms to about 1.0 milligrams of active compound per kilogram body weight. Effective doses may be extrapolated from dose-response curves derived from in vitro or animal model test systems. Dose ranges disclosed in Zapol and Frostell, supra, and higher can be therapeutically employed.

EXAMPLE 1

Effect of NO Inhalation on Coagulation Time Rabbit and Human

In this study we have focused on shorttime effects on coagulation parameters in rabbits from inhaled nitric oxide (NO) in the dose range 3–300 ppm, and in three human subjects exposed to 30 ppm NO. The studies were performed at the Department of Clinical Physiology at Uppsala University Hospital, Uppsala, Sweden.

MATERIAL AND METHODS a) Rabbits

The study was approved by the Animal Ethics Committee of Uppsala University. New Zealand White rabbits of both sexes (n=11), with a mean body weight of 3.1±0.2 kg were studied. Neurolept anesthesia (1) was administered before intubation and maintained throughout the experiment. Artificial ventilation was given with a Siemens 900C ventilator (Siemens-Elema, Lund, Swden) with an inspired oxygen fraction ($FIO_2$) of 0.3. After a 30 minutes stabilization period a double tidal volume was delivered to reopen any collapsed lung tissue. An inflation pressure (Pmax) limit was set at 25 cm $H_2O$. Respiratory mechanics, i.e. respiratory resistance (Rrs) and lung compliance (Crs), mean arterial pressure (MAP), heart rate, end-tidal $CO_2$ ($EtCO_2$) and peripheral oxygen saturation ($SpO_2$) were obtained at baseline and at the end of the NO inhalation period. NO 1000 parts per million (ppm) in nitrogen ($N_2$) was obtained from AGA Medical Gas AS, Lidingo, Sweden. The desired NO concentration in inspired gas was achieved by mixing NO in $N_2$, oxygen, and air at the low-pressure gas supply inlet of the ventilator as described previously (3).

Bleeding time was measured repeatedly in a rabbit ear template model as described by Merton and Thomas (2), using a standardized incision (Minilancet, CCS, Borlange, Sweden). Blood was blotted with a filter paper at 10 sec intervals until no blood stain on the filter paper appeared. Blood was sampled from an ear vein for the measurement of simplastin coagulation time (in vitro measurement), fibrinogen concentration and platelet count immediately before each measurement of the bleeding time.

Our protocol was to measure bleeding time and sample blood at 1) baseline; 2) after 15 minutes of inhaling NO 3 ppm (n=2), NO 30 ppm (n=7), or NO 300 ppm (n=2); 3) after 30 minutes from terminating NO inhalation. The measurement during NO inhalation was begun after 15 minutes and NO inhalation continued until the measurement was completed.

b) Humans

The Human Ethics Committee of Uppsala University has approved studies on shortterm (<30 minutes) exposure with inhaled nitric oxide 80 ppm NO or less in human volunteers. The subjects were studied at least 2 hours after a light meal, were subjectively lung healthy and studied awake sitting in a chair. They were presently taking no medication and had not been taking aspirin for at least 10 days before the study. We measured $SpO_2$ and heart rate with pulse oximetry.

The subject wore a nose-clip and was connected via a mouth-piece to a non-rebreathing circuit consisting of a 10 liter reservoir bag and one-way valves to isolate inspired from expired gas. Expired gas was scavenged and discarded. Inspired gas was passed through a one-way valve and a soda lime cannister which removed the $NO_2$ formed in the system, and the gas was then inhaled through a mouth piece. NO 1000 ppm in $N_2$ was mixed with $N_2$ and $O_2$ using volumetrically calibrated flowmeters, to a gas mixture with an $FIO_2$ of 0.21. The $FIO_2$ was continuously monitored with a Beckman $O_2$ analyzer (OM 11, Beckman Instruments AB, Stockholm, Sweden). The subjects started to breathe through the system 3 minutes before we obtained baseline measurements, then the $N_2$ flow was reduced to allow for the addition of NO in $N_2$ to the desired NO concentration. The system has been described previously (4). Concentrations of NO and $NO_2$ was checked on-line with chemiluminescence (Tecan 502, Switzerland).

Samples of venous blood was withdrawn immediately before measuring bleeding time; and were analyzed for platelet count, fibrinogen concentration and in vitro coagulation time. The bleeding time was measured with a standardized incision (Simplastin II, Organon Tika, NC, USA) on the ventral aspect of the left forearm. Blood was blotted with a filter paper at 10 sec intervals until no blood stain on the filter paper appeared.

Our protocol was to measure bleeding time and sample blood at 1) baseline; 2) after 15 minutes of inhaling NO 30 ppm; and 3) after 60 minutes from terminating NO inhalation. NO inhalation was continued until the measurement of bleeding time was completed.

STATISTICS

Statistical analysis was performed using t-test for paired data (SigmaStat, Jandel Scientific, Erkrath, Germany). Data are given as mean ±SEM.

RESULTS a) Rabbits

The addition of NO to inspired gas did not affect heart rate, MAP, $EtCO_2$ $SpO_2$, Pmax, Rrs, Crs (data not shown). There were no significant alterations in platelet count, fibrinogen concentration and in vitro coagulation time during the study (data not shown). Bleeding time was 49±6 seconds during baseline conditions and increased after 15 minutes of NO inhalation 30 ppm to 72±9 seconds (ratio 1.54 ±0.2, p=0.015). Finally, 30 minutes after terminating NO inhalation the bleeding time was 53±4 seconds (ratio 1.13 ±0.2). The two rabbits exposed to only 3 ppm NO increased their mean bleeding time ratio to 1.48 and then returned to baseline 30 minutes after terminating NO. Inhalation of 300 ppm NO in two rabbits increased the bleeding time ratio to 2.44, which remained high 30 minutes after terminating NO at 3.19; see also FIG. 1.

b) Humans

No discomfort was experienced by any subject during NO inhalation. There were no change in heart rate or $SpO_2$ during the study. There were no significant alterations in platelet count, fibrinogen concentration and in vitro coagulation time during the study (data not shown). Bleeding tine ratio increased to mean 1.4 after 15 minutes of breathing NO 30 ppm, and returned towards baseline 60 minutes after terminating NO inhalation. See also Table 1.

Table 1

Bleeding time in seconds before, during NO inhalation after 15 minutes of inhaling 30 ppm NO, and 60 minutes after terminating NO inhalation. Bleeding time ratio in parenthesis, the actual bleeding time divided with the baseline value.

|  | Before | During NO | After NO |
| --- | --- | --- | --- |
| subject 1 | 610 | 910 (1.51) | 641 (1.05) |
| subject 2 | 262 | 381 (1.42) | 280 (1.04) |
| subject 3 | 372 | 487 (1.31) | 392 (1.05) |

This study confirms that inhalation of nitric oxide prolongs the bleeding time in rabbits and humans. The prolongation of bleeding time was significant after 15 minutes of inhalation of 30 ppm NO in rabbits, and could be clearly demonstrated in human volunteers at the same dose for the same time.

The delivered dose of NO was validated on-line with chemiluminescence during the study. The effect was reversible within 30 minutes from turning NO off. The effect appears to be dose dependent, and at 300 ppm NO in 2 rabbits exposed for 30 minutes the effect was still present at 30 minutes from turning NO off (FIG. 1).

When platelets pass the pulmonary circulation they could vary well absorb some of tile inhaled NO, and in this way have the aggregation and adhesion tendency somewhat supressed by an increase of cyclic GMP content in these platelets (4). The observation in this study of a prolonged (>30 minutes) effect of NO inhalation when inspiring 300 ppm NO necessitates an additional mechanism for the effect. Inhalation of NO must increase a pool of NO or NO releasing compounds in blood, that can release NO slowly for many minutes after NO inhalation has been stopped.

REFERENCES

1. Flecknell PA. In: Laboratory animal anesthesia. Academic Press 1987; 128–129.
2. Merton RE,, Thomas DP. Experimental studies on the relative efficacy of dermatan sulphate and heparin as antithrombotic agents. *Thromb Haemosts* 1987; 58: 839–842.
3. Hogman M, Frostell C, Arnberg H, Hedenstierna G. Inhalation of nitric oxide modulates metacholine-induced bronchoconstriction in the rabbit. *Eur Respir J* 1993; 6:177–180.
4. Stamler J, Loscalzo J. The antiplatelet effects of organic nitrates and related nitroso compounds in vitro and in vivo and their relevance to cardiovascular disorders. *J Am Coll Cardiol* 1991; 18: 1529–1536.

EXAMPLE 2

The Human Ethics Committee of the Karolinska Institute has approved the use of nitric oxide inhalation in patients with critical pulmonary hypertension. For details of equipment see appendix.

The patient, a fullterm baby girl weighing 3.1 kg, was born at a local county hospital. Immediately after delivery a diagnosis of congenital diaphragmatic hernia (CDH) was suspected due to absent breath sounds over the left hemithorax, scaphoid abdomen and displaced heart sounds. Initial Apgar scores were 2-6-8 at 1, 5 and 10 minutes respectively. The child was immediately transferred (20 km) to our neonatal intensive care unit. On arrival the patient had a peripheral oxygen saturation of 70–75% breathing spontaneously with supplemental oxygen on a face mask. Preoperative stabilization was achieved using standard procedures including nasotracheal intubation, mechanical ventilation, acid-basecorrection and volume replacement. A chest radiograph verified the diagnosis of CDH, showing the spleen, ventricle and small intestine with a part of the transverse colon in the heft hemithorax. The time from arrival to surgical repair was 3 hours. The child was anaesthetized using fentanyl 25 microg/kg, middazolam 0.15 mg/kg, and pancuronium 0.15 mg/kg, and ventilated mechanically with $O_2$ in air (50–70% $O_2$). A typical posterior defect in the left diaphragm was observed and sutured. A drain was placed in the left pleural space. Postoperatively the child was readmitted to the NICU and kept deeply sedated.

Adequate gas exchange could be achieved using 50% inspired oxygen fraction ($FIO_2$), peak inspiratory pressure (PIP)/positive end expiratory pressure (PEEP) of 20/2 cm H₂O, respiratory frequency 40 per minute, inspiratory; expiratory ratio as 1:2. No vasoactive drugs were needed at this point.

After a period of 8 hours of stable circulation and gas exchange, a deterioration in oxygenation was noted. This deterioration progressed despite increased ventilatory support and meticulous correction of acid-base balance. At 20 hours postoperatively no further benefit could be achieved from increasing ventilatory settings from $FIO_2$ 1.0, PIP/PEEP 36/4, and respiratory frequency 80 per minute. An echocardiographic examination showed evidence for pulmonary hypertension, with an elevated systemic right ventricular pressure (i.e. a pressure gradient of 65 mmHG between the right ventricle and atrium, as estimated by a tricuspid insufficiency jet). The velocity profile in the pulmonary artery showed typical notching and the ratio of the preejection period over acceleration time was increased (PEP/AT=2.5). The ductus arteriosus was patent and during 80% of the cardiac cycle flow as directed from the pulmonary artery to the aorta. Pharmacologic pulmonary vasodilation was then attempted using a prostacyclin (5–20 nanog/kg per min) infusion. In order to support systemic blood pressure volume loading (5% albumin 10 ml/kg) and a dopamine infusion (7–15 microg/kg per min) were administered. After eight hours of suboptimal but acceptable gasexchange a dramatic decline in oxygenation was observed and progressed for the next 45 minutes. Finally no peripheral arterial saturation could be measured and deep cyanosis with gasping was noted. Repeated periods of manual ventilation with 100% $O_2$ for a total of 20 minutes did not improve the situation. The endotracheal tube was not dislodged. Breath sounds over the thorax were unchanged. A postductal arterial blood gas displayed severe metabolic acidosis (Base Excess −29 mmolL), pronounced hypercarbia and a postductal $PaO_2$ of only 16 mmHG. However, despite obvious respiratory failure the arterial blood pressure was still maintained and the heart rate was at or above 100 beats per min.

Inhalation of nitric oxide

Since conventional treatment had failed and circulatory collapse was deemed imminent a decision was made to attempt to restore gas exchange with the addition of NO inhalation. No 20 ppm was added to inspred gas and 40 ml of Tris-sdiumbicarbonate buffer solution (Tribonate, Pharmacia, Uppsala, Sweden) was given over 10 minutes in order to counter the severe metabolic acidosis. A gradual increase of SpO2 was observed over the next 20 minutes, and repeated arterial blood gas samples confirmed restoration of gas exchange. During this time the prostacyclin infusion was discontinued and NO administration weaned down to 10 ppm.

Over the next 75 minutes ventilatory support could be reduced to an FIO2 of 0.7, peak airway pressure/PEEP to 20/0 cm H2O and respiratory frequency 70 per min. A repeated echocardiographic assessment showed similar findings compared to the previous examination with the except of a reduced PEP/AT (1.25).

A severe hypocalcemia (lowest ionized serum calcium level of 0.55 mmOlxL-1), complicated by a period of a functional 2:1 atrioventricular block (corrected QT time: 0.54 s) combined with hypotension, developed after resuscitation and restoration of circulation and gas exchange.

The first attempt to discontinue NO inhalation was performed 40 hours after initiating this treatment. At this point electrolyte and acid-base disorders had been corrected and the $FIO_2$ had successfully been reduced to 0.25. The discontinuation test was performed during simultaneous monitoring with echocardiography. Wti 5 ppm NO still administered a reduction of the tricuspid insufficiency and a decrease in the maximal pressure difference between the right bentricl and atrium (35 mmHG) was noted. The velocity profile of the pulmonary artery did no longer demonstrate any apparent notching and the PEP/AT had normalized (0.8) The ductus arteriosus had closed. No alterations in gas exchange or echocardiographic parameters appeared within 15 minutes after discontinuation of NO inhalation. Since significant pulmonary hypertension was still evident it was decided to continue NO inhalation for another 12 hours. During this period it was possible to further reduce $FIO_2$ to 0.21. As no deterioration in gas exchange could be detected during the second discontinuation test, NO treatment was stopped. Five hours later the dopamine infusion could be discontinued.

During the entire period no other pulmonary pathology than the left sided pulmonary hypoplasia could be seen on repeated chest radiographs. At a follow up echocardi-graphy later in the recovery phase a restrictive perimembranous VSD with an estimated peak gradient of 30 mmHG could be identified.

The child was extubated 5 days later, and was discharged from hospital 3 weeks later.

Plasma S-nitrosoprotein Levels (a) Plasma levels of S-nitrosoprotein were 5.9 μm after 30 min of inhaled NO gas 5 ppm.

(b) Plasma levels of S-nitrosoprotein fell after discontinuation of inhaled NO; levels were 5.3 μm 30 minutes after discontinuing NO.

(c) Plasma levels were 2.1 μm 120 minutes after discontinuing NO.

These data establish that inhaled NO gas results in a pool or reservoir of plasma (blood) S-nitrosoprotein that decreases over time after NO administration is discontinued.

EXAMPLE 3

MATERIALS AND METHODS

The study was approved by the Human Ethics Committee of Uppsala University, as well as the Drug Regulatory Affairs Office for Sweden. A total of 31 adults divided into 4 groups were studied, sometimes on several occasions as detailed below.

Group 1: non-smoking hyperreative subjects (n=6), mean age 39±9 years, 1 man and 5 women.

Group 2: non-smoking hyperreactive subjects (n=6), mean age 31±10 years, 3 men and 3 women. Hyperreactivity was defined as decrease in airway conductance after a methacholine provocation test a few days preceding the study. The subjects were not taking any drug as a prophylactic or as part of a treatment.

Group 3: patients (n=6) with a diagnosis of chronic bronchitis in stable condition, being on continuous medication, with a sGaw less than 1.2 (kPa's); a mean age of 56±12 years, 3 men and 3 women.

Group 4: patients (n−10) with a diagnosis of asthma in stable condition on continuous medication; with a sGaw less than 1.2 (kPa's); a mean age of 41±11 years, 7 men and 3 women.

Mixing, administration and monitoring of inspired gas including NO.

During the study, the subject was seated in the body plethysmography, wore a nose-clip and was connected via a mouth-piece to a non-rebreathing circuit consisting of a 10 liter reservoir bag and one-way valves to isolate inspired from expired gas. The inspired gas was a mixture of $O_2$ and $N_2$ to produce the correct inspired $O_2$ fraction ($FIO_2$). The $FIO_2$ was continuously monitored with a Beckman $O_2$ analyzer (OM 11, Beckman Instruments AB, Stockholm, Sweden) and maintained at 21% $O_2$ througout the study. Using volumetrically calibrated flowmeters, varying quantities of NO mixed with $N_2$ were substituted for pure $N_2$ to obtain the desired inspired NO concentration at constant $FIO_2$ of 21%. Inspired gas was passed through a canister containing soda lime, placed closed to the one-way valve, in order to absorb and thereby minimize any $NO_2$ content. NO in $N_2$ was obtained from AGA Specialgas (Lidingo, Sweden) as a mixture of 240 ppm NO in pure $N_2$. Chemiluminescence analysis (Model 8841, Monitor Labs, Englewood, Colo.) demonstrated the desired NO concentration as 80 ppm $\pm 5\%$ with $NO_2$ in this mixture after the $NO_2$ absorbing canister as less than 0.3 ppm.

Plasma S-Nitrosoprotein Levels

Time dependent increase in plasma S-nitrosoproteins before inhaled NO
(a) before inhaled NO gas plasma level=2.5 $\mu m$
(b) after inhaled NO gas, plasma level=3.46 $\mu m$ These data establish that inhaled NO gas results in accumulation of a pool or reservoir of nitric oxide plasma (blood) S-nitrosoprotein in the systemic bloodstream upon inhalation administration of NO.

What is claimed is:

1. A method for systemically treating a patient to inhibit blood platelet aggregation and coagulation comprising systemically treating a patient for blood platelet aggregation and coagulation by administering by the inhalation route to the lung of a patient in need thereof an amount of a compound effective for systemically inhibiting blood platelet aggregation and coagulation selected from the group consisting of nitric oxide and a compound that delivers nitric oxide.

2. The method of claim 1 wherein the nitric oxide delivering compound is selected from the group of S-nitrosothiols, S-nitroso-proteins, NONOnates, iron nitrosyls, iron nitrosyls with thiolate ligands, thionitrites, thionitrates, sydnonimines, furoxans, nitrosonium salts, organic nitrates and organic nitrites.

3. A method for treating acute respiratory distress syndrome in a patient in need thereof comprising administering to the lung of a patient suffering from acute respiratory distress syndrome an amount of a pharmaceutical composition which comprises a compound effective for treating acute respiratory distress syndrome in said patient selected from the group consisting of nitric oxide and a compound that delivers nitric oxide.

4. The method of claim 3 wherein the nitric oxide delivering compound is selected from the group of S-nitrosothiols; S-nitroso-proteins, NONOnates, iron nitrosyls, iron nitrosyls with thiolate ligands, thionitrites, thionitrates, sydnonimines, furoxans, nitrosonium salts, organic nitrates and organic nitrites.

5. A method for establishing an increased level of nitric oxide in the systemic circulation of a patient in need thereof comprising administering by the inhalation route to the lung of said patient in need thereof an amount of a pharmaceutical composition which comprises a compound effective for establishing an increased level of nitric oxide in the systemic circulation of said patient selected from the group consisting of nitric oxide and a compound that delivers nitric oxide.

6. The method of claim 5 wherein the nitric oxide delivering compound is selected from the group of S-nitrosothiols, S-nitroso-proteins, NONOnates, iron nitrosyls, iron nitrosyls with thiolate ligands, thionitrites, thionitrates, sydnonimines, furoxans, nitrosonium salts, organic nitrates and organic nitrites.

* * * * *